United States Patent
Eyster et al.

(10) Patent No.: US 12,351,284 B2
(45) Date of Patent: *Jul. 8, 2025

(54) FORMABLE AQUATIC COVERINGS FOR PREVENTING BIOFOULING

(71) Applicant: Biofouling Technologies, Inc., Aberdeen, NC (US)

(72) Inventors: Fletcher Eyster, Jupiter, FL (US); Fred Zucker, Jupiter, FL (US)

(73) Assignee: BIOFOULING TECHNOLOGIES, INC., Aberdeen, NC (US)

( * ) Notice: Subject to any disclaimer, the term of this patent is extended or adjusted under 35 U.S.C. 154(b) by 73 days.

This patent is subject to a terminal disclaimer.

(21) Appl. No.: 18/131,081

(22) Filed: Apr. 5, 2023

(65) Prior Publication Data
US 2023/0242224 A1    Aug. 3, 2023

Related U.S. Application Data

(63) Continuation of application No. 17/035,886, filed on Sep. 29, 2020, now Pat. No. 11,623,716, which is a continuation of application No. 15/802,593, filed on Nov. 3, 2017, now abandoned, which is a continuation of application No. 13/973,516, filed on Aug. 22, 2013, now abandoned, which is a continuation-in-part of application No. 13/177,098, filed on Jul. 6, 2011, now Pat. No. 8,541,439.

(60) Provisional application No. 61/361,725, filed on Jul. 6, 2010.

(51) Int. Cl.
| | | |
|---|---|---|
| *B63B 59/04* | (2006.01) | |
| *A01N 25/34* | (2006.01) | |
| *B63B 17/00* | (2006.01) | |
| *B63H 20/36* | (2006.01) | |
| *C07D 498/18* | (2006.01) | |
| *C09D 5/16* | (2006.01) | |
| *E02B 17/00* | (2006.01) | |

(52) U.S. Cl.
CPC ............ *B63B 59/045* (2013.01); *A01N 25/34* (2013.01); *B63B 59/04* (2013.01); *C07D 498/18* (2013.01); *C09D 5/1625* (2013.01); *E02B 17/0017* (2013.01); *B63B 2017/0045* (2013.01); *B63H 20/36* (2013.01); *Y10T 428/1345* (2015.01); *Y10T 428/24273* (2015.01)

(58) Field of Classification Search
CPC .... A01N 25/34; B63B 59/045; C09D 5/1625; E02B 17/0017; Y10T 428/24273
See application file for complete search history.

(56) References Cited

U.S. PATENT DOCUMENTS

| | | |
|---|---|---|
| 3,220,374 A | 11/1965 | Sloan |
| 3,505,758 A | 4/1970 | Willisford |
| 3,587,508 A | 6/1971 | Pearce |
| 3,870,875 A | 3/1975 | Altimus |
| 4,046,094 A | 9/1977 | Preiser et al. |
| 4,253,877 A * | 3/1981 | Miale .................. B01J 13/10 264/4.4 |
| 4,375,199 A | 3/1983 | Graeme-Barber |
| 4,865,909 A | 9/1989 | Manniso |
| 4,869,016 A | 9/1989 | Diprose et al. |
| 4,998,496 A | 3/1991 | Shaw, III |
| 5,009,757 A | 4/1991 | Riffe et al. |
| 5,072,683 A | 12/1991 | Colonia |
| 5,315,949 A | 5/1994 | Bradley |
| 5,346,598 A | 9/1994 | Riffe et al. |
| 5,354,603 A | 10/1994 | Errede |
| 5,423,631 A | 6/1995 | Inoue |
| 5,552,057 A | 9/1996 | Hughes et al. |
| 6,152,064 A | 11/2000 | Morton |
| 6,183,646 B1 | 2/2001 | Williams et al. |
| 6,247,195 B1 | 6/2001 | O'Brien et al. |
| 6,303,078 B1 | 10/2001 | Shimizu et al. |
| 6,547,952 B1 | 4/2003 | Staerzl |
| 6,609,938 B1 | 8/2003 | Pither |
| 7,390,560 B2 | 6/2008 | Wallach |

(Continued)

FOREIGN PATENT DOCUMENTS

| | | |
|---|---|---|
| CL | 200700725 | 9/2007 |
| CN | 1056537 A | 11/1991 |

(Continued)

OTHER PUBLICATIONS

Webster's New World Dictionary of the American Language, Second College Edition, David B. Guralnik, Editor in Chief, The World Publishing Company, 1972, p. 1127, "prevent". (Year: 1972).
Akhondi et al; The Performance and Fouling Control of Submerged Hollow Fiber (HF) Systems: A Review; Applied Sciene [online], 2017 [Retrieved on Dec. 20, 2019], vol. 7, 765, pp. 1-39, [Retrieved from the Internet: https://doi.org/10.3390/app7080765].

*Primary Examiner* — Mina Haghighatian
*Assistant Examiner* — Nathan W Schlientz
(74) *Attorney, Agent, or Firm* — Nelson Mullins Riley & Scarborough LLP

(57) ABSTRACT

The instant invention describes an anti-biofouling structure for placement onto structures or surfaces that are exposed to aquatic environments. Embedded within the anti-biofouling structure are agents that can diffuse out of the structure and prevent the formation and/or accumulation of plant and animal species build-up that creates biofouling. The instant invention also describes a system for preventing biofouling of an object stored in an aquatic environment which includes the anti-biofouling structure, and a protective cover element constructed and arranged to fit various structures, such as boat propellers.

17 Claims, 13 Drawing Sheets

(56) References Cited

U.S. PATENT DOCUMENTS

| | | |
|---|---|---|
| 7,811,513 B2 | 10/2010 | Johnson et al. |
| 8,541,439 B2 | 9/2013 | Eyster et al. |
| 8,591,740 B2 | 11/2013 | Nupnau et al. |
| 10,457,570 B2 | 10/2019 | Kuik et al. |
| 11,623,716 B2 * | 4/2023 | Eyster ............... E02B 17/0017 428/35.5 |
| 2001/0052364 A1 | 12/2001 | Walker |
| 2002/0030011 A1 | 3/2002 | Constantine et al. |
| 2003/0203991 A1 | 10/2003 | Schottman et al. |
| 2004/0018583 A1 | 1/2004 | Ho et al. |
| 2006/0024344 A1 | 2/2006 | Matos et al. |
| 2006/0037896 A1 | 2/2006 | Cote et al. |
| 2006/0189686 A1 | 8/2006 | Martensson |
| 2007/0068605 A1 | 3/2007 | Statnikov |
| 2008/0020657 A1 | 1/2008 | Williams |
| 2008/0302713 A1 | 12/2008 | Patrick |
| 2009/0185867 A1 | 7/2009 | Masters et al. |
| 2009/0239009 A1 | 9/2009 | Tanaka |
| 2009/0304621 A1 | 12/2009 | Cavitt et al. |
| 2010/0006018 A1 | 1/2010 | Lathem |
| 2010/0051527 A1 | 3/2010 | Frandsen |
| 2010/0051545 A1 | 3/2010 | Johnson et al. |
| 2011/0036240 A1 | 2/2011 | Taylor et al. |
| 2011/0120362 A1 | 5/2011 | Costas |
| 2011/0305895 A1 | 12/2011 | Roth et al. |
| 2012/0009236 A1 | 1/2012 | Eyster et al. |
| 2012/0018312 A1 | 1/2012 | Yamamoto et al. |
| 2013/0139744 A1 | 6/2013 | Le Buzit |
| 2013/0175222 A1 | 7/2013 | Spittle et al. |
| 2013/0337201 A1 | 12/2013 | Eyster et al. |
| 2014/0141263 A1 | 5/2014 | Jones et al. |
| 2014/0216093 A1 | 8/2014 | Kaiser et al. |
| 2014/0291253 A1 | 10/2014 | Coulter |
| 2014/0339148 A1 | 11/2014 | Hu |
| 2016/0009925 A1 | 1/2016 | Matsuki |
| 2016/0122745 A1 | 5/2016 | Jeffs et al. |
| 2017/0173588 A1 | 6/2017 | Tang et al. |
| 2017/0217549 A9 | 8/2017 | Eyster et al. |
| 2017/0349455 A1 | 12/2017 | Katz |
| 2018/0050774 A1 | 2/2018 | Eyster et al. |
| 2019/0174749 A1 | 6/2019 | Yeung et al. |
| 2019/0364886 A1 | 12/2019 | Steele et al. |
| 2021/0009242 A1 | 1/2021 | Eyster et al. |

FOREIGN PATENT DOCUMENTS

| | | |
|---|---|---|
| CN | 1769597 A | 5/2006 |
| CN | 105209187 A | 12/2015 |
| CN | 106660082 A | 5/2017 |
| DE | 29514526 U1 | 1/1997 |
| EP | 0384655 A1 | 8/1990 |
| EP | 631637 A1 | 1/1995 |
| EP | 1084947 A1 | 3/2001 |
| EP | 1918190 A1 | 5/2008 |
| EP | 1981659 A1 | 10/2008 |
| EP | 2218636 A2 | 8/2010 |
| EP | 3458420 A1 | 3/2019 |
| FR | 2536363 A | 5/1984 |
| GB | 614799 A | 12/1948 |
| GB | 754812 A | 8/1956 |
| GB | 851902 A | 10/1960 |
| GB | 865083 A | 4/1961 |
| JP | H06-098662 A | 4/1994 |
| JP | 2000-143414 A | 5/2000 |
| JP | 2001-089577 A | 4/2001 |
| JP | 2003-189784 A | 7/2003 |
| JP | 2007-186933 A | 7/2007 |
| JP | 4256319 B2 | 4/2009 |
| JP | 5161201 B2 | 3/2013 |
| KR | 200194214 Y1 | 9/2000 |
| KR | 100572354 B1 | 4/2006 |
| KR | 101158675 B1 | 6/2012 |
| KR | 20180043689 A | 4/2018 |
| WO | WO 96/11839 A1 | 4/1996 |
| WO | 2006/03740 A1 | 1/2006 |
| WO | WO 2012/006333 A1 | 1/2012 |
| WO | WO 2015/027129 A2 | 2/2015 |
| WO | 2017/109287 A1 | 6/2017 |
| WO | WO 2018/001359 A1 | 1/2018 |
| WO | 2020/093015 A1 | 5/2020 |
| ZA | 926542 B | 2/1993 |

* cited by examiner

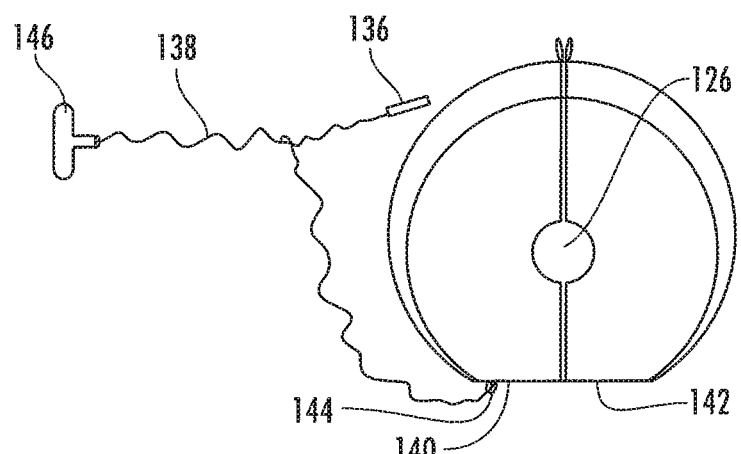
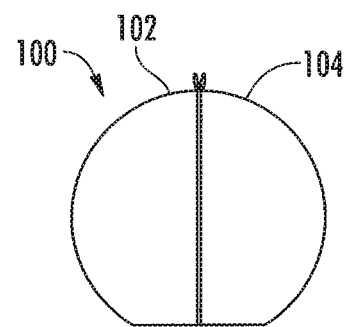
FIG. 18          FIG. 17
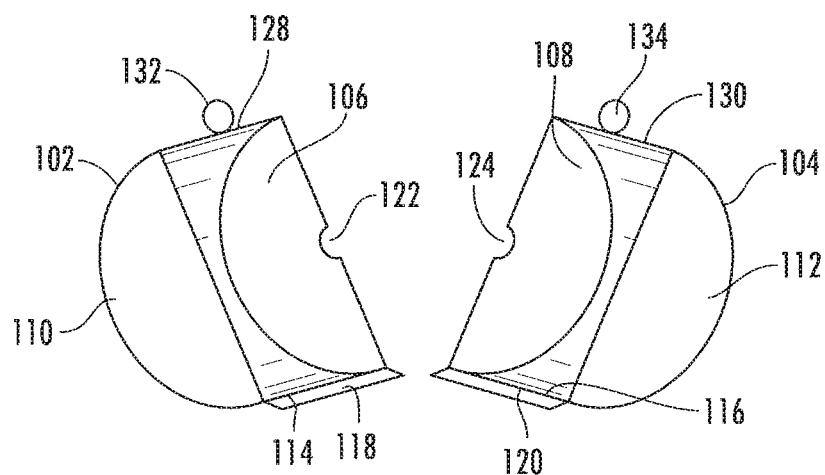
FIG. 19

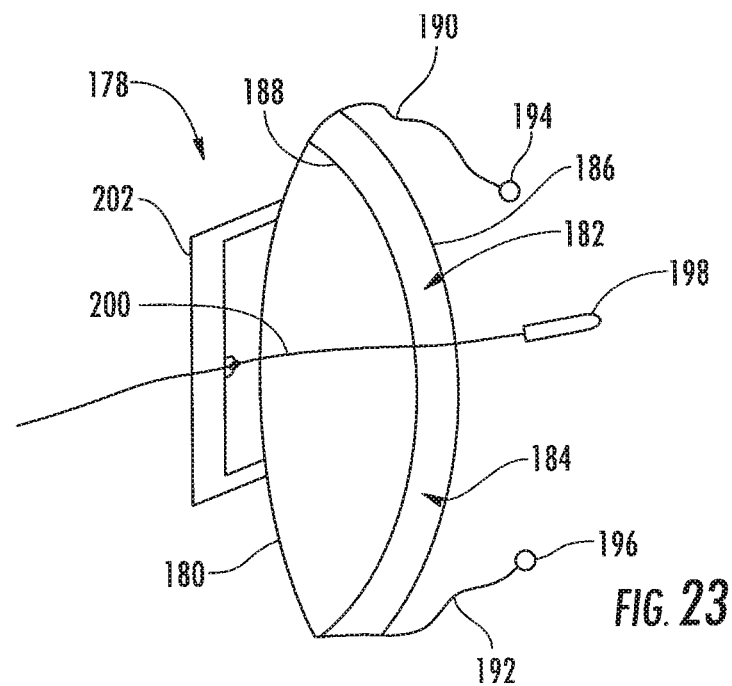
FIG. 23
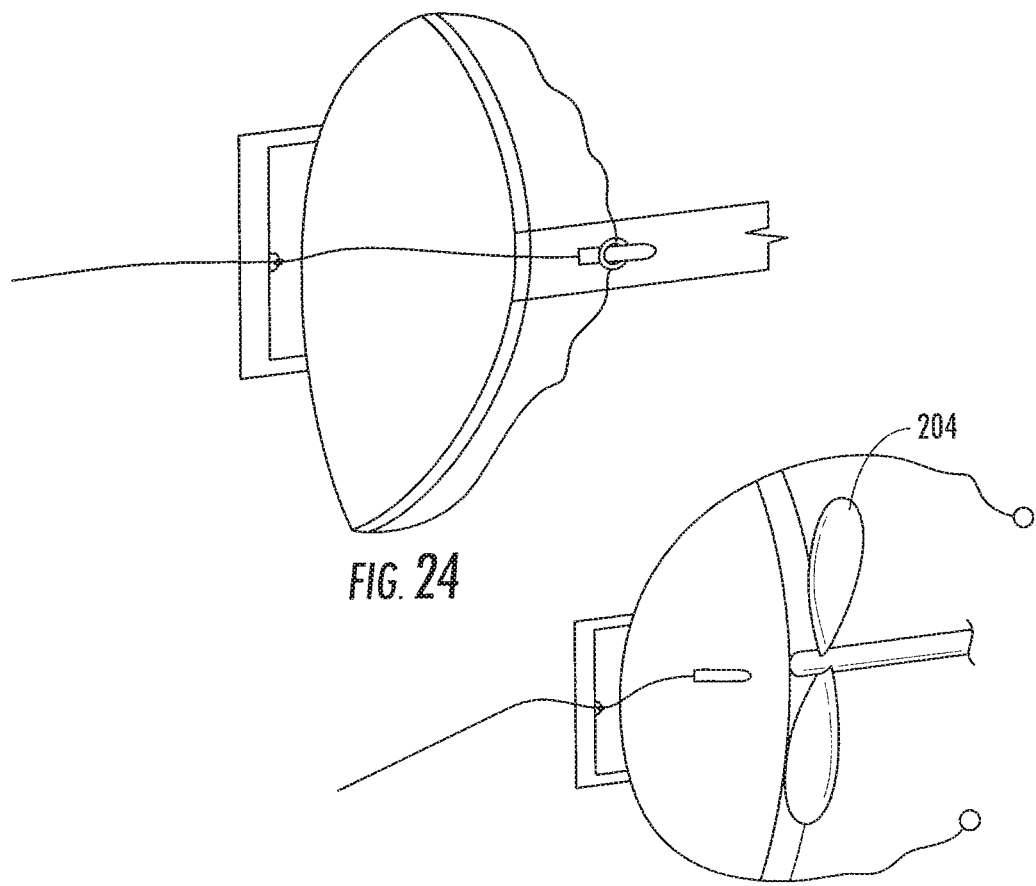
FIG. 24
FIG. 25

FORMABLE AQUATIC COVERINGS FOR PREVENTING BIOFOULING

CROSS REFERENCE TO RELATED APPLICATIONS

This application is a continuation of U.S. application Ser. No. 17/035,886, filed on Sep. 29, 2020, entitled "Formable Aquatic Coverings for Preventing Biofouling", which is a continuation of U.S. application Ser. No. 15/802,593, filed on Nov. 3, 2017, entitled "Formable Aquatic Coverings for Preventing Biofouling", which is a continuation of U.S. application Ser. No. 13/973,516, filed on Aug. 22, 2013, entitled "Formable Aquatic Coverings for Preventing Biofouling", which is a continuation-in-part of U.S. Application Ser. No. 13/177,098, filed on Jul. 6, 2011, entitled "Formable Aquatic Coverings for Preventing Biofouling" which issued as U.S. Pat. No. 8,541,439 on Sep. 24, 2013, which application claims the benefit of priority under 35 U.S.C. 119 (e) to the U.S. Provisional Application No. 61/361,725, entitled "Formable Aquatic Coverings for Preventing Biofouling" filed Jul. 6, 2010, the entire contents of which aforementioned applications are incorporated herein by reference.

FIELD OF THE INVENTION

The present invention relates to the protection of structures from damage as a result of continuous exposure to aquatic environments; more particularly to devices which attach to submerged structures, thereby preventing formation of biofouling; and even more particularly to a system for preventing aquatic biofouling containing a propeller enclosure and a formable and disposable propeller glove having anti-aquatic biofouling properties.

BACKGROUND OF THE INVENTION

The growth and attachment of various marine organisms on structures in aquatic environments, known as biofouling, is a significant problem for numerous industries, including the boating and shipping industry, the oil and gas industry, and the fishing industry. Most surfaces, such as those associated with boat hulls, underwater cables, oil rig platforms, buoys, and fishing nets, which are exposed to coastal, harbor or ocean waters eventually become colonized by animal species, such as barnacles, mussels, bryozoans, hydroids, tunicates, tubeworms, sea squirts, and various plant species. Biofouling results from the interaction of polymeric adhesives produced by the plant and animal species with the substrates for which they are attached. Despite the appearance of simplicity, the process of biofouling is actually complex and involves numerous interactions with many types of microorganisms and macroorganisms.

While biofouling creates ecological problems by distributing native plant and animal species to non-native environments, its economic effects are of greater concern. Large amounts of biofouling on ships result in corrosion of the surfaces and the eventual deterioration of the ship. Large amounts of macroorganisms build-up also causes increases in the roughness of the ship's surface such that the ship experiences greater frictional resistance, decreased maneuverability, and increased drag, resulting in increased fuel consumption. Recreational boaters suffer from the same problems, as barnacles and other animals attach to propellers submerged in water. Navigational buoys or pier posts containing surfaces with large amounts of biofouling are subjected to increased stress resulting from increased weight. This increased stress often results in decreasing the useful life of the structures and necessitating continuous replacement.

Various methods have been used in reducing biofouling build-up. One of the more common methods, particularly in the boating and shipping industry, is scraping. However, scraping is labor intensive and environmental issues have been raised over the concerns that scraping results in the increased spread of invasive species. Therefore, there exists a need for devices that eliminate or reduce the amount of biofouling of surfaces exposed to water.

DESCRIPTION OF THE PRIOR ART

One strategy for protecting objects in contact with water and preventing aquatic biofouling includes the use of physical coverings. These coverings act as protective devices by shielding or separating the structures from the water. For example, U.S. Pat. No. 3,220,374 discloses a marine protective device. The invention is directed towards a unique means and method of protecting marine equipment from the corrosive action of the water and/or marine growth when the boat is not in use.

U.S. Pat. No. 3,587,508 discloses an outdrive protective apparatus for easy attachment to a boat. The apparatus protects the outdrive of an inboard-outboard motor from marine growth when the boat is not in use. A bag is placed around the outdrive unit for easy attachment to the transom of a boat in a manner which provides a watertight seal between the bag and the transom and around the outdrive unit.

U.S. Pat. No. 3,870,875 discloses a cover for covering the propeller and rear drive assembly of an outboard-inboard motor boat. The cover has an electric taillight mounted to the rear of the cover and which can be electrically connected to the taillight wire of a boat trailer when the boat is mounted on the boat trailer for towing on a roadway. The light serves as a warning to motorists approaching the boat and boat trailer from the rear.

U.S. Pat. No. 4,998,496 discloses a shroud for a marine propulsion system which includes a waterproof shroud body that can be fastened to the transom of a boat to surround the outboard portion of the propulsion system. Locking and sealing mechanisms secure the shroud to the boat transom in water-tight engagement and a submersible pump is operable to remove water from the shroud body so that the propulsion system is effectively in dry dock.

U.S. Pat. No. 5,072,683 discloses a drainable protective boat motor bag apparatus including a boot defining a bag for fitting over the propeller and stem of an outdrive of a motor mounted on the stern of a boat. The bag includes a channel extending from the mouth to the closed end of the bag for receipt of an open ended hose such that, once the bag has been positioned over the stem, a hose may be inserted for pumping of residual from such bag. A tie string may be incorporated around the mouth of the bag for tying it to the stem and, if desirable, a separate protective sack may be included for covering the propeller blades to protect them from direct exposure to the bag itself.

U.S. Pat. No. 5,315,949 discloses an apparatus for protectively covering a motor prop of a boat. The cover includes an adjustable collar, a flexible, opaque bag, and an adjustable collar draw line. The bag has an open top end attached to the collar. A closed bottom end of the bag is opposed to the top end, and has a weight attached thereto. The adjustable collar draw line of the collar is such that with the bag placed over the outcropping, the open end of the bag may be closed around the outcropping by pulling the adjustable collar draw line. The collar includes a locking slot for locking the adjustable collar draw line in place around the outcropping. A manipulation handle removably attaches to the collar for facilitating the placement and removal of the cover onto and off of the outcropping. With the cover in place over the outcropping, water and light are prevented from entering the interior of the bag, whereby water borne life forms such as filter feeding creatures and plant life cannot thrive within the cover. As such, the motor prop is kept virtually free of water borne life forms while the motor prop is covered.

U.S. Pat. No. 6,152,064 discloses a protective propeller cover. The cover includes a flexible sleeve into which buoyant material is placed to provide a buoyant enclosure. A flexible propeller cover portion is secured to the flexible sleeve, and the end of the cover is releasably secured about the propeller. The buoyant enclosure is positioned adjacent to the propeller and extends above the water line when the propeller is positioned beneath the water line. The buoyant enclosure serves to protect swimmers from direct contact with the propeller when swimming in proximity to the boat. The protective propeller cover apparatus further serves to protect the propeller during transport or storage. The protective propeller cover apparatus further serves as an anchor cover when the boat is underway. The protective propeller cover apparatus further serves as an emergency flotation device.

U.S. Pat. No. 6,609,938 discloses a propeller protector slipper which is used on inboard and outboard motors of boats that are anchored, drifting, aground, docked, in storage, or out of water in transit. The propeller protector slipper ensures protection for the propeller from elements that cause pitting and damage to the propeller, as well as minimizing propeller related injuries. The protector propeller slipper also provides a gage for projecting the distance of the propeller of a trailered boat from a following vehicle.

U.S. Publication No. 2008/0020657 discloses an apparatus for protecting the outdrive of a watercraft. The apparatus comprises a locating member adapted for attachment to the underside of the marlin board of the watercraft and a shroud engageable with the locating member to provide an enclosure about the outdrive. The shroud is buoyant and can be floated into sliding engagement with the locating member. The shroud has an opening which is closed upon engagement of the shroud with the transom of the watercraft to prevent ingress of water into the interior of the shroud. A connection means and the locking means are provided for releasably connecting the shroud to the locating member.

In addition to the use of physical coverings as illustrated above, other strategies have been employed in efforts to reduce biofouling. U.S. Publication No. 2009/0185867 discloses a system and method for reducing vortex-induced vibration and drag about a marine element. The system includes, but is not limited to, a shell rotatably mounted about the marine element, the shell having opposing edges defining a longitudinal gap configured to allow the shell to snap around at least a portion of the marine element. A fin can be positioned along each opposing edge of the longitudinal gap, wherein each fin can extend outwardly from the shell. The fins can be positioned on the shell so as to reduce vortex-induced vibration and minimize drag on the marine element. One or more antifouling agents can be disposed on, in, or about at least a portion of the shell, the fins, or a combination thereof.

U.S. Pat. No. 7,390,560 discloses a coating system for defouling a substrate. The system includes a ship hull, immersed in water or seawater for long periods of time. The system comprises a conductive layer, an antifouling layer and a means for providing an energy pulse to the conductive layer. The conductive layer comprises polymers, such as carbon filled polyethylene, which are electrically conductive. The antifouling layer comprises polymers, such as polydimethylsiloxane, which have a low surface free energy. The layers are designed such that when the conductive layer is exposed to a pulse of electrical, acoustic or microwave energy or combinations thereof, said conductive layer separates from said antifouling layer.

SUMMARY OF THE INVENTION

The instant invention describes an anti-biofouling structure for placement onto structures or surfaces that are exposed to aquatic environments. Embedded within the anti-biofouling structure are agents that can diffuse out of the structure and prevent the formation and/or accumulation of plant and animal species. In a particular embodiment, the anti-biofouling structure covers the blades of a boat propeller. Embedded within this structure is the anti-biofouling agent sirolimus. The instant invention also describes a system for preventing biofouling of an object stored in an aquatic environment. The system includes the anti-biofouling structure and a protective cover element constructed and arranged to fit various objects, such as a boat propeller.

In one embodiment, the instant invention describes an anti-biofouling structure for placement onto an object exposed to aquatic environments comprising a formable covering material for securing to an object which is in contact with an aquatic environment. The formable covering material comprises at least one anti-biofouling agent, whereby securing of the object with said material results in preventing the formation of biofouling along the surface of the object. The instant invention also describes a system for preventing biofouling of objects which are exposed to aquatic environments comprising a cover having a material containing one or more anti-biofouling agents. The cover has a front surface, an expandable body portion which is traversable between a first position and a second expanded position, an interior portion sized and shaped to enclose an object which is exposed to aquatic environments, and one or more securing members for securing said cover to said object. The system also includes a formable covering material for securing to an object which is in contact with an aquatic environment. The formable covering material comprises at least one anti-biofouling agent, whereby securing of the object with said material results in preventing the formation of biofouling along the surface of the object.

In an alternative embodiment, the system includes a first rigid member made of a material containing one or more anti-biofouling materials hingedly securable to a second rigid member. The second rigid member is made of a material containing one or more anti-biofouling agents. Each of the rigid members contains an interior which is sized and shaped to receive an object which is exposed to an aquatic environment. The cover further includes one or more securing members for securing the cover to the object. The system also includes a formable covering material for securing to an object which is in contact with an aquatic environment. The formable covering material comprises at least one anti-biofouling agent, whereby securing of the object with said material results in preventing the formation of biofouling along the surface of the object.

In another alternative embodiment, the system for preventing biofouling of objects which are exposed to aquatic environments comprises a flexible cover containing one or more anti-biofouling materials. The cover contains a first face partially connected to a second face and an interior portion sized and shaped to receive a boat propeller. The second face contains a slatted portion terminating in an opening which is sized and shaped to receive a shaft of the propeller. The first face and the second face contain a first member of a hook and loop fastener securing system. The system further includes a strap containing a second member of a hook and loop fastener securing system. The strap is sized and shaped to secure to the first member of a hook and loop fastener securing system.

Accordingly, it is a primary objective of the instant invention to provide an anti-biofouling structure which prevents the formation of biofouling on an object which is exposed to an aquatic environment.

It is a further objective of the instant invention to provide an anti-biofouling structure which contains anti-fouling agent dispensing strips.

It is yet another objective of the instant invention to provide an anti-biofouling structure which contains anti-fouling agents within reservoirs and/or are microencapsulated.

It is a still further objective of the invention to provide an anti-biofouling structure in which the anti-fouling agent is sirolimus.

It is a further objective of the instant invention to provide a system for preventing biofouling of an object stored in an aquatic environment which includes an anti-biofouling structure and a protective enclosure element.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 17 illustrates a front view of an alternative embodiment of the anti-biofouling structure in the form of a claim shell configuration;

FIG. 18 is a rear view of the alternative embodiment of the biofouling structure illustrated in FIG. 17;

FIG. 19 is a perspective view of the embodiment of the biofouling structure illustrated in FIG. 17, illustrating the components of the clamshell;

FIG. 23 is a side view of an alternative embodiment of the anti-biofouling structure in the form of collapsible bag-like configuration;

FIG. 24 is a side view of the embodiment of the anti-biofouling structure shown in FIG. 23, illustrating the bag in a closed, sealed configuration;

FIG. 25 is a side view of the anti-biofouling structure shown in FIG. 24, illustrating the bag being removed from covering of a propeller.

DETAILED DESCRIPTION OF THE INVENTION

Figure 1:
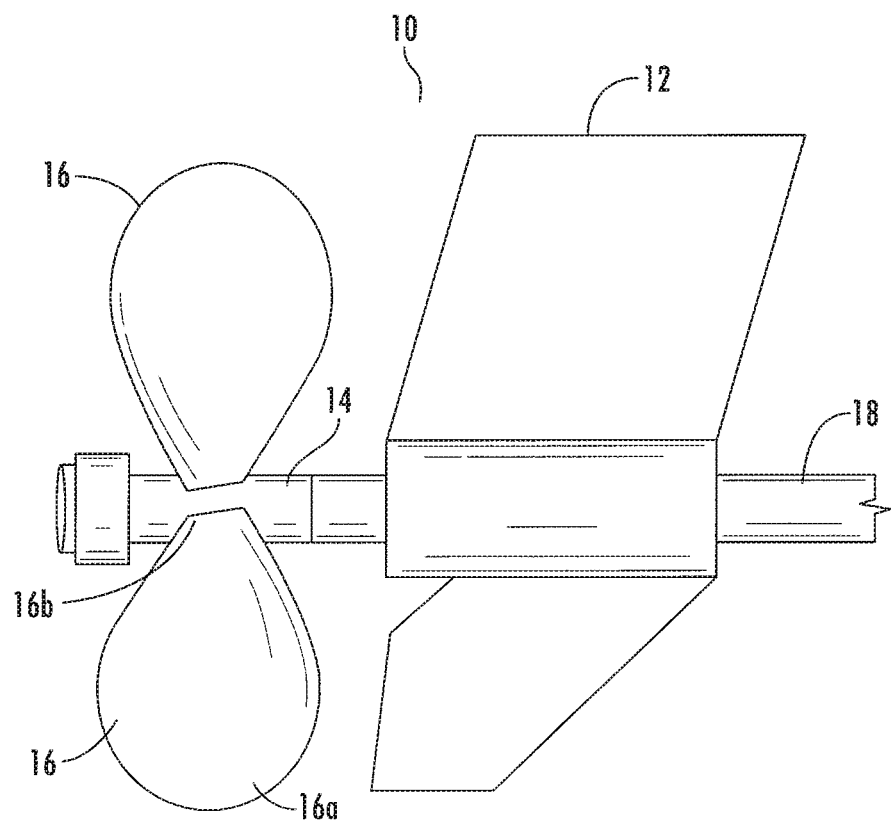
FIG. 1 is a simplified illustration of a typical boat propeller system.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

The instant invention describes an anti-biofouling structure for placement onto structures or surfaces that are exposed to aquatic environments. While the anti-biofouling structure will be described in the specification as being useful on a boat propeller, one of skill in the art would recognize that the anti-biofouling structure is not limited to boat propellers and may be applied to numerous other structures placed in aquatic environments, such as but not limited to pier posts, buoys, oil rig structures, boat docks, and the like. Accordingly, FIG. 1 is a simplified illustration of a typical boat propeller 10 having a motor drive system 12. Attached to the hub 14 are multiple propeller blades 16. A shaft 18, which interconnects the hub 14 to the outboard motor drive system 12, provides a mechanism for rotational movement of the propeller blades 16.

Figure 2:
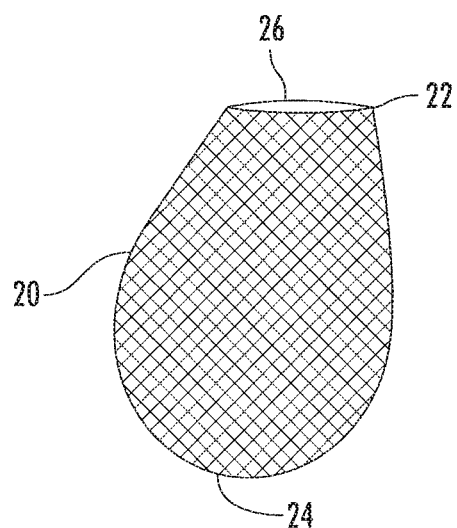
FIG. 2 illustrates a particular embodiment of the anti-biofouling structure of the instant invention.
Figure 3:
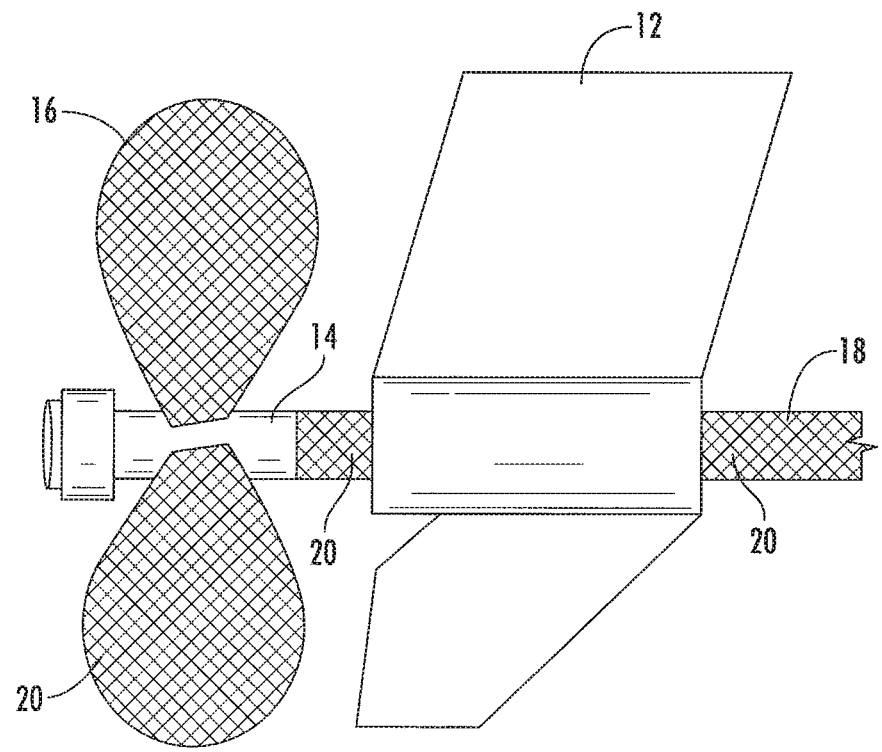
FIG. 3 illustrates placement of the anti-bio Wing structure to the propellers and propeller shaft.

FIG. 2 illustrates a particular embodiment of the anti-biofouling structure 20 in the form of a boat propeller sock. The boat propeller sock 20 has a first end 22 and a second end 24. The boat propeller sock 20 is placed on the propeller 16 by inserting the distal end 16a of propeller 16 into the first end 22 of the boat propeller sock 20 through opening 26. As the boat propeller sock 20 is positioned over the propeller 16, the boat propeller sock 20 is aligned such that the first end 22 rests at or near the proximal portion 16b of the propeller 16 and the second end 24 of the boat propeller sock 20 rests at or near the distal portion 16a of the propeller 16. In order to fit securely, the boat propeller sock 20 can be constructed to include the same general contoured shape as the propeller. FIG. 3 illustrates placement of the boat propeller sock 20 on the multiple propeller blades 16.

Figure 4:
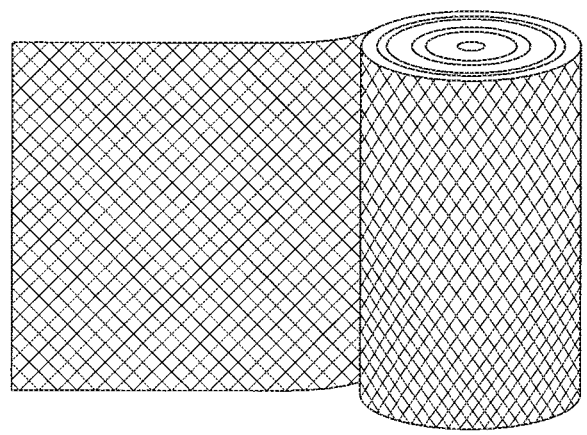
FIG. 4 illustrates the anti-biofouling structure in the form of a rolled up sheet.
Figure 5:
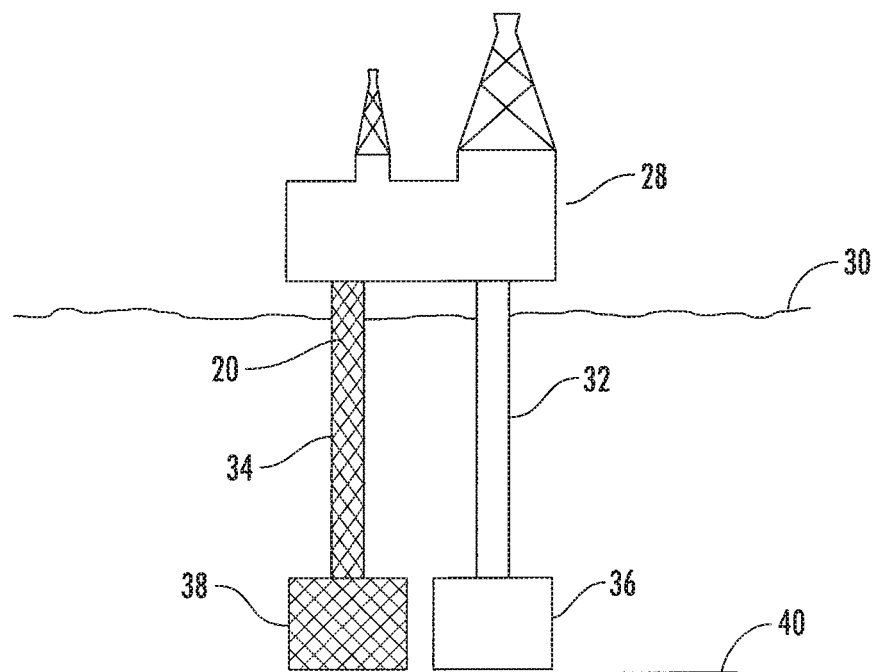
FIG. 5 illustrates a general schematic of an oil rig used to excavate oil reserves in deep waters with the anti-biofouling structure attached to a portion of the rig.
Figure 6:
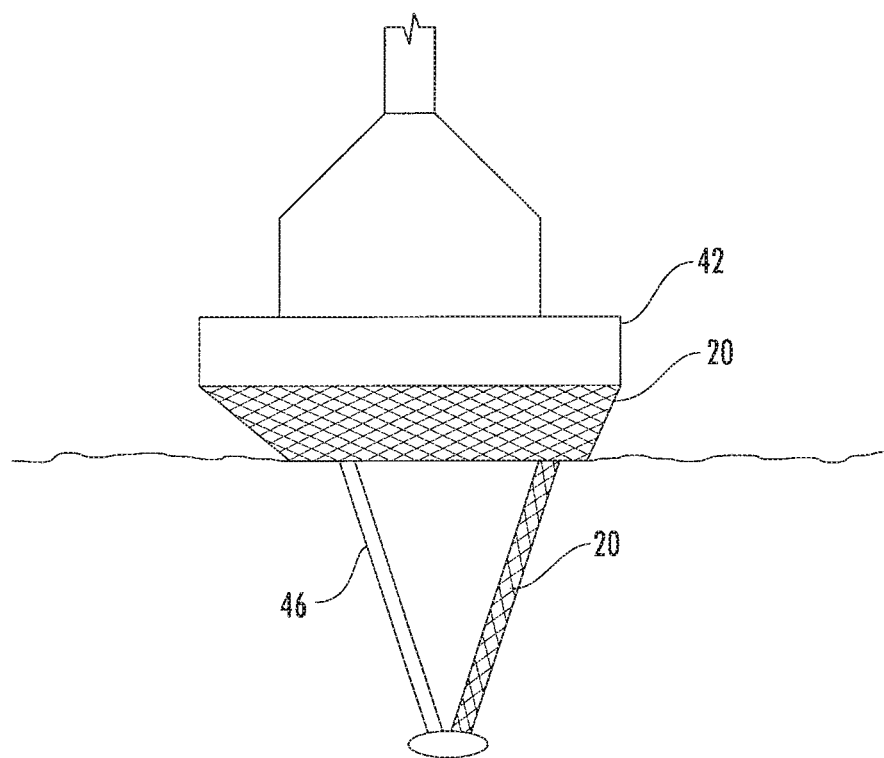
FIG. 6 illustrates the use of the anti-biofouling structure with a buoy.

While the instant invention has been described in the form of a boat propeller sock, the anti-biofouling structure 20 can be shaped to fit any structure. FIG. 4 illustrates the anti-biofouling structure 20 in the form of a rolled up sheet. As such, the anti-biofouling structure 20 can be placed onto various types of aquatic structures, such as netting, in-take pipes, and sewage pipes. FIG. 5 illustrates a general schematic of an oil rig used to excavate oil reserves in deep waters. The oil rig 28 sits above ocean water 30. Support columns 32 and 34 terminate at bases 36 and 38, respectively, resting at the wound level 40 below the ocean surface. To extend the life of the support and base structures, the anti-biofouling structure 20 can be either embedded within or, as illustrated, simply wrapped around the support column and base. FIG. 6 illustrates the use of the anti-biofouling structure 20 with a buoy 42. The anti-biofouling structure 20 can be attached to the portion of the buoy that is near or in direct contact with the aquatic environment to prevent the accumulation of biofouling within those areas. Additionally, anti-biofouling structure 20 can be attached to any of the cables 46 which anchor the buoy 42 to the sea floor.

FIGS. 7A, 7B, 8A, and 8B, illustrate particular embodiments of the anti-biofouling structure 20 which comprise a lattice-like or fenestrate arrangement. Alternatively, biofouling structure 20 may be in the form of a mesh. The anti-biofouling structure 20 contains a plurality of horizontally positioned elements 50 interweaved with a plurality of vertically positioned elements 52. Both the horizontally positioned elements and the vertically positioned elements may be arranged diagonally, thus forming a crisscross pattern, see FIGS. 7A and 7B, or alternatively in a parallel fashion relative to each other, thereby forming right angles, see FIGS. 8A and 8B. While the figures illustrate a significant spacing between the individual horizontal and/or vertical elements, the spacing can be decreased in order to form an anti-biofouling structure 20 which has a tightly knit, weaved pattern with little or no spacing in between. In a preferred embodiment, the horizontally positioned elements 50 and the vertically positioned elements 52, such as fibers, are made of natural or synthetic plastics, but could be made of other materials such as metals, nylons, cotton, or combinations thereof. The anti-biofouling structure 20 may also be constructed of a biodegradable material such that continued exposure to the aquatic environment results in environmentally friendly degradation. Whichever type of materials are used, the anti-biofouling structure 20 may be constructed such that the structure is formable such that it is capable of being expanded three-dimensionally, radially, longitudinally, or combinations thereof. This constriction allows positioning over an object so that the anti-biofouling structure 20 mirrors the contour of the surface of the object for which it is attached thereto.

In order to impart anti-biofouling characteristics, attached to or embedded within the horizontally positioned elements 50 and/or the vertically positioned elements 52 are agents which prevent biofouling. In a preferred embodiment, the anti-biofouling agent is sirolimus having the following chemical structure:

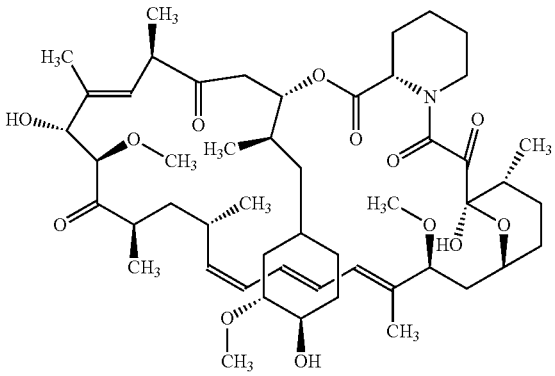 [SMILES: CO[C@H]1C[C@H]2CC[C@@H](C)[C@@](O)(O2)C(=O)C(=O)N2CCCC[C@H]2C(=O)O[C@H]([C@H](C)CC2CC[C@@H](O)[C@H](OC)C2)CC(=O)[C@H](C)/C=C(\C)[C@@H](O)[C@@H](OC)C(=O)[C@H](C)C[C@H](C)\C=C/C=C/C=C/1C]

Sirolimus, also known as rapamycin, is a macrocyclic triene antibiotic originally isolated from the soil microorganism *Streptomyces hygroscopicus*. Since first being used as an anti-fungal antibiotic, use of Sirolimus has expanded to other fields of medicine. Sirolimus is commonly used as a powerful immmunosuppressant drug for preventing rejection after organ transplant surgeries. Research also indicates that Sirolimus can act as a cell-cycle inhibitor, blocking the natural progression of the cell cycle. Other anti-biofouling agents, such as biocides, known one of skill in the art may be used as well, either individually, or in combination. Anti-biofouling agents which prevent both microfouling, such as biofilm formation and bacterial attachment, and macrofouling, such as attachment of large organisms, including barnacles or mussels, are preferable.

Figures 7A, 7B:
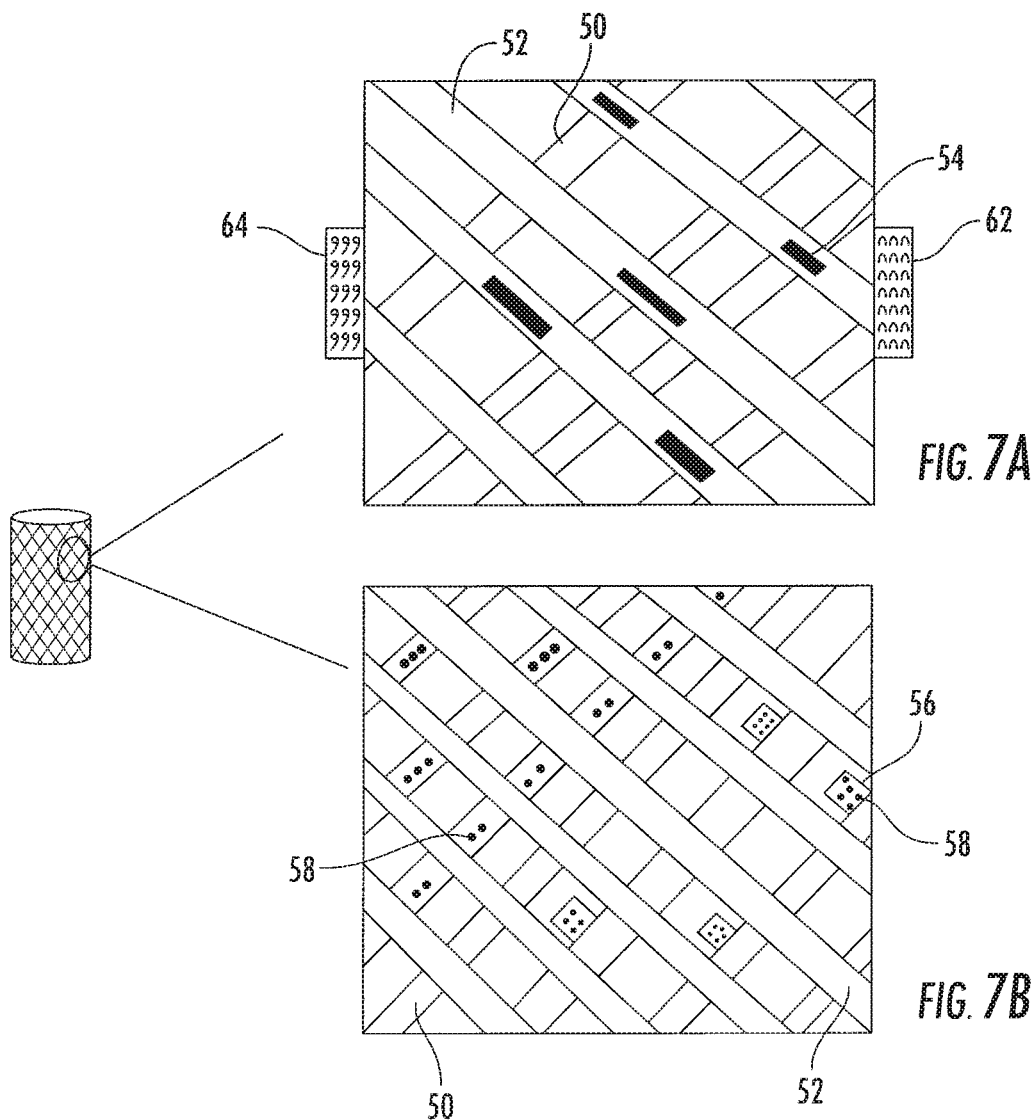
FIG. 7A illustrates a particular embodiment of the anti-biofouling structure in which the diagonally arranged horizontal and vertical elements contain anti-fouling agent dispensing strips.
FIG. 7B illustrates a particular embodiment of the anti-biofouling structure in which the diagonally arranged horizontal and vertical elements contain anti-fouling agents within reservoirs and/or are microencapsulated.
Figure 8A:
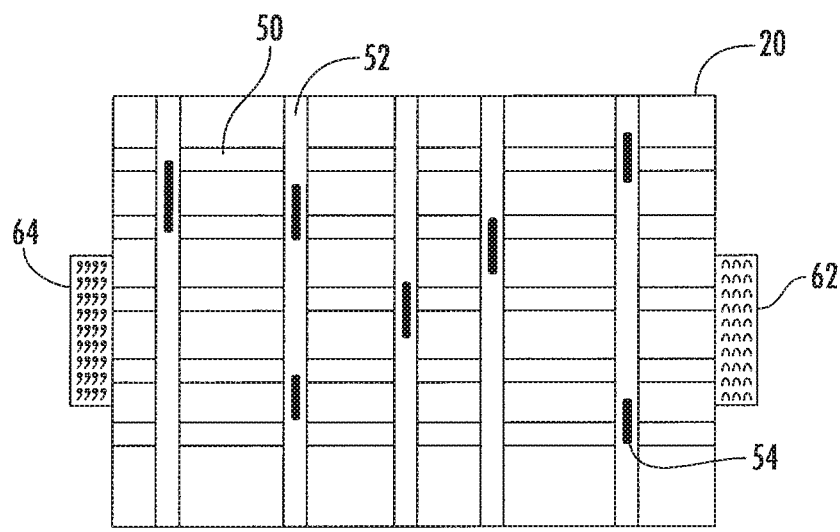
FIG. 8A illustrates a particular embodiment of the anti-biofouling structure in which the horizontal and vertical elements contain anti-fouling agent dispensing strips.
Figure 8B:
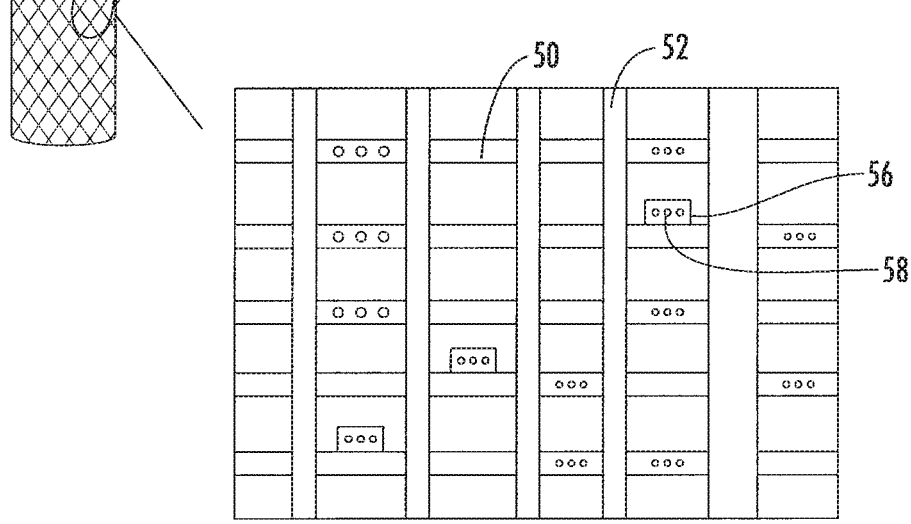
FIG. 8B illustrates a particular embodiment of the anti-biofouling structure in which the horizontal and vertical elements contain anti-fouling agents within reservoirs and/or are microencapsulated.

Referring to FIGS. 7A and 8A, attached to the horizontally positioned element 50 and the vertically positioned element 52 are strips 54. The strips 54 contain various concentrations of sirolimus and are constructed in such a manner as to leach or diffuse out of the strip 54 and into the external environment, thus preventing the various plant and animal species from attaching or establishing a presence on the anti-biofouling structure 20. FIGS. 7B and 8B illustrate an alternative embodiment of the anti-biofouling structure 20. The anti-biofouling structure 20 has a reservoir 56 which contains free or microencapsulated sirolimus. The microencapsulation provides a mechanism in which the sirolimus is diffused or released into the environment in a time dependant manner. The sirolimus filled microcapsules 58 can be embedded into the horizontally positioned element 50 and the vertically positioned element 52 without the use of the reservoir 56. While these mechanisms described above may be the preferred methods for embedding sirolimus within the anti-biofouling structure 20, other methods of inserting the anti-fouling agent, such as the use of spray-on applications, as known to one of skill in the art is contemplated. Additionally, the anti-biofouling structure 20 need not contain the vertical or horizontal elements but may rather be made of a pliable sheet which contains the anti-fouling agent embedded therein. To provide a securing mechanism, the anti-biofouling structure 20 can include fastening elements, such as but not limited to loop 62 and hook 64 type fasteners, such as VELCRO, or snaps, buttons, glue strips, or zippers.

Figure 9:
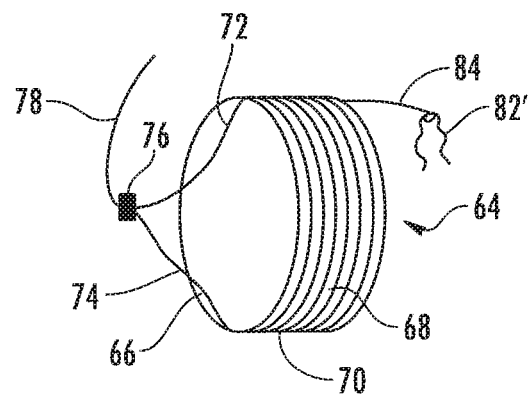
FIG. 9 illustrates a particular embodiment of the protective enclosure element in the form of an expandable bag propeller cover.

The instant invention further contemplates a system for preventing biofouling of an object stored in an aquatic environment. The system includes the anti-biofouling structure as previously described and a protective enclosure element, which may comprise a material containing one or more anti-biofouling agents. FIG. 9 illustrates a particular embodiment of the protective enclosure element 64 in the form of an expandable bag. Protective enclosure element 64 has a generally circular shaped front surface 66 and an expandable/collapsible body portion 68. A portion of the expandable/collapsible body contains accordion-like infoldings 70 which allow the protective enclosure element 64 to be traversed between a first resting or collapsed position, see FIG. 9, and a second fully extended position, see FIG. 11, or multiple positions between the first and second positions.

Figure 10:
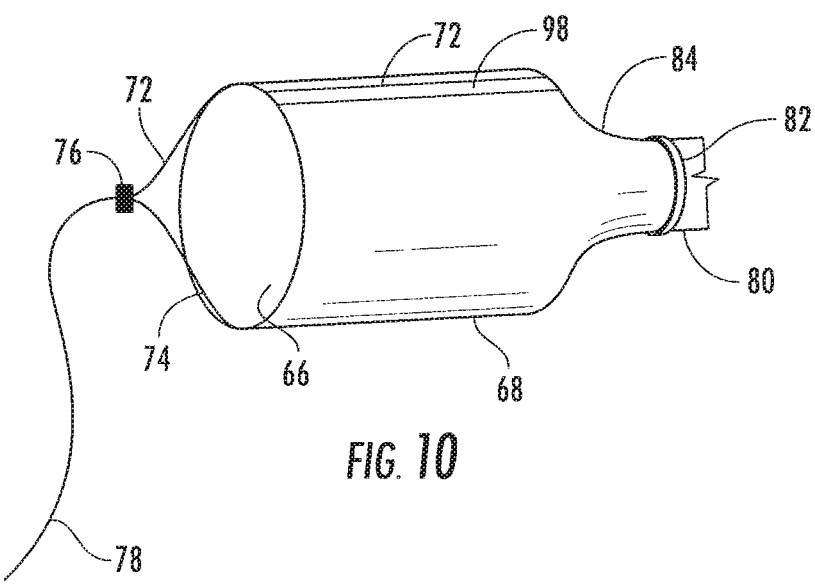
FIG. 10 illustrates the protective enclosure element in an expanded position.
Figure 11:
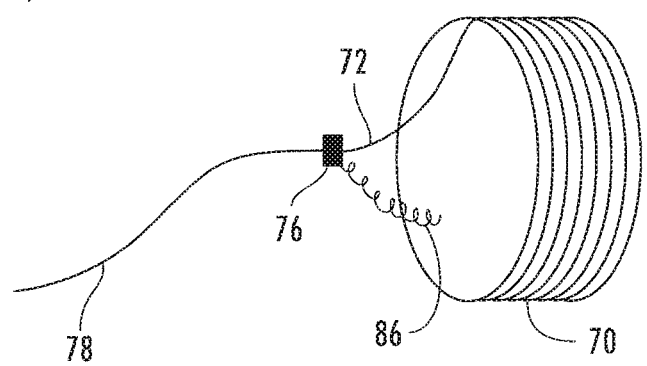
FIG. 11 illustrates an alternative embodiment of the protective enclosure element.

Attached to the protective enclosure element 64 is a first cable 72 and a second cable 74. The first cable 72 and the second cable 74 which can be made of rope, plastic, or preferably of stainless steel, connect via attaching element 76, such as a clip or swage, to a single securing cable or lanyard 78. When in the extended form, the securing end 80 of the protective enclosure element 64 is exposed and secures the protective enclosure element 64 to a structure or object, such as an exposed shaft of a boat propeller, by way of fastening element 82, see FIG. 10. Fastening element 82 can be connected to the protective enclosure element 64 through a securing string 84. FIG. 11 illustrates an alternative embodiment of the protective enclosure element 64. This embodiment contains the same features as described previously; however, the second cable has a coiled portion 86.

Figure 12:
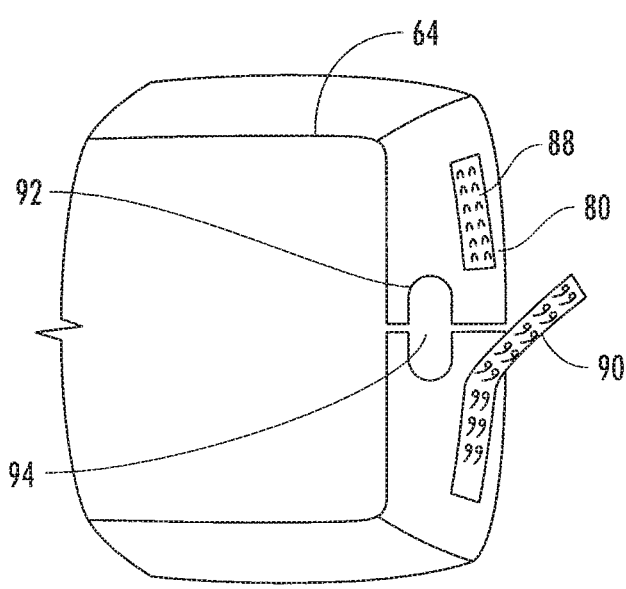
FIG. 12 is a perspective view of the back end of the extended protective enclosure element.

FIG. 12 is a perspective view of the fully extended protective enclosure element 64. As illustrated, the securing end 80 contains the fastening elements 88 and 90. The fastening elements 88 and 90 are illustrated as a loop and hook type fastener, i.e. VELCRO, however, the fastening elements may also include snaps, clasps, clip, buttons, zippers, or other fastening type devices known to one of skill in the art. Although not necessary, the securing end 80 may be designed to contain portions 92 and 94 which provide a place in which securing end 80 may be attached to the external aquatic structure.

Figure 15:
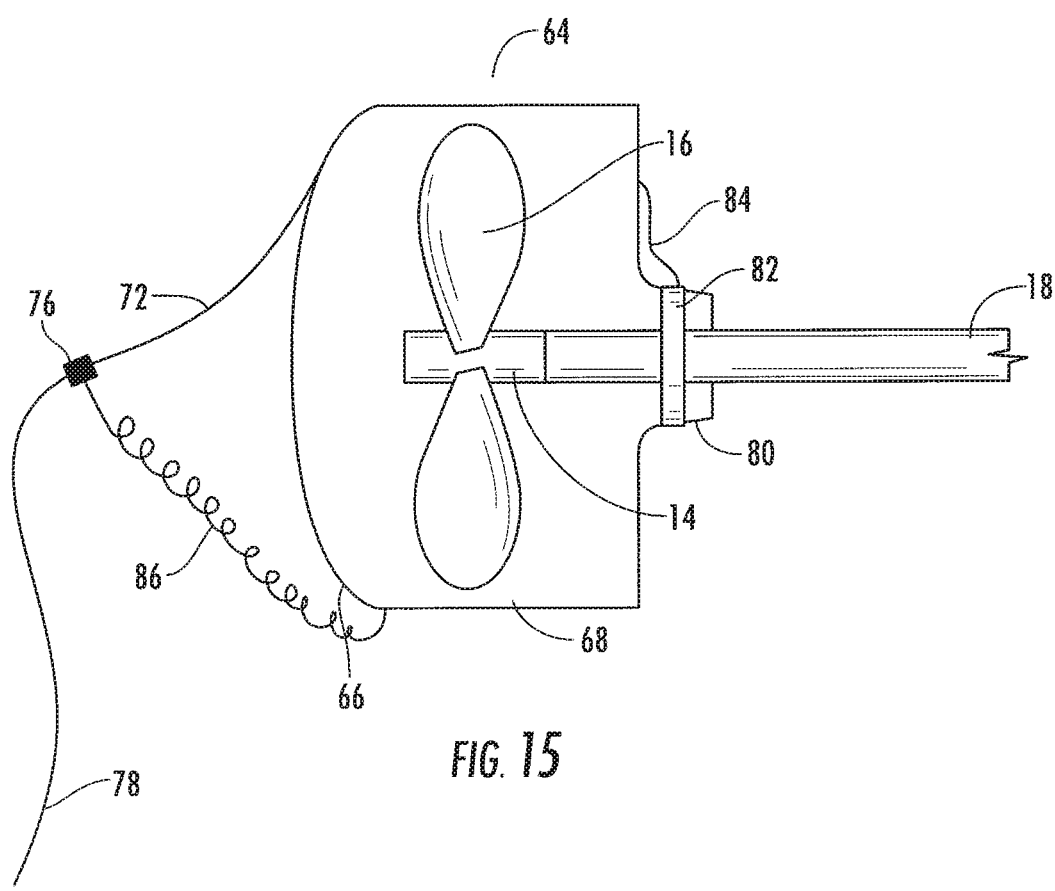
FIG. 15 illustrates the protective enclosure element positioned over a boat propeller and secured to the boat propeller shaft.
Figure 16:
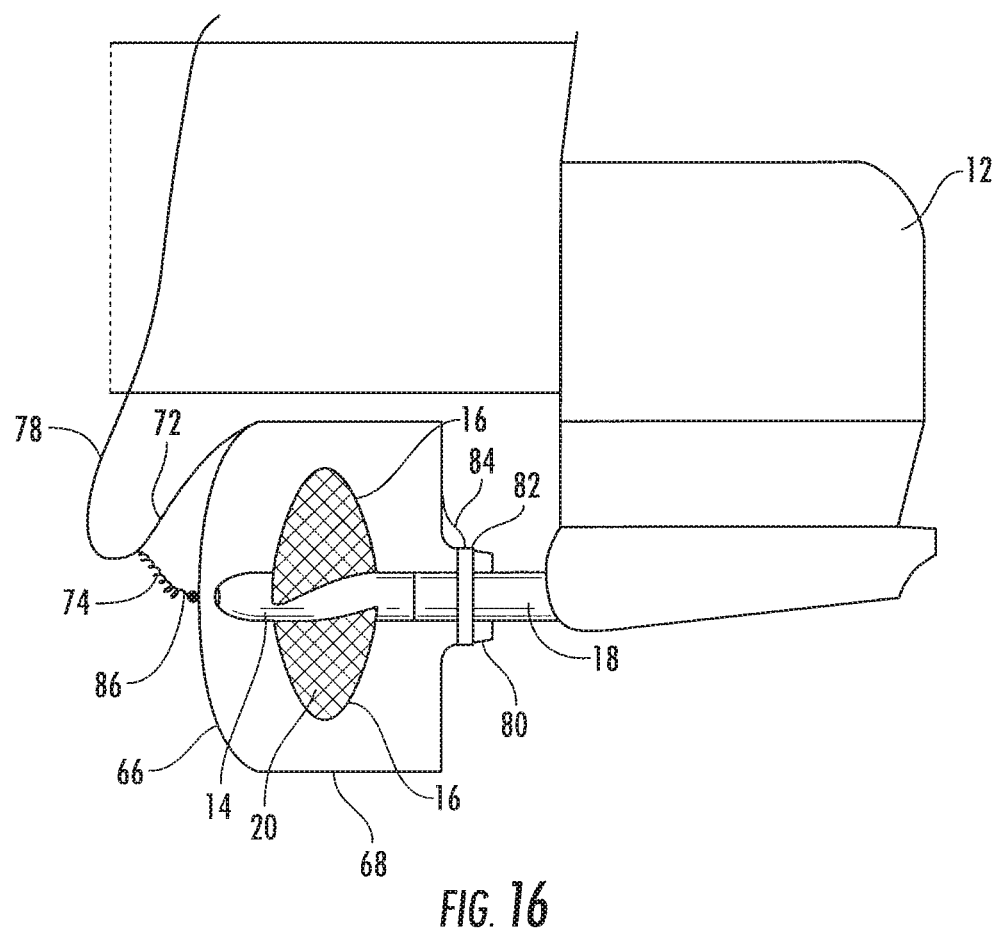
FIG. 16 illustrates both the protective enclosure element positioned over a boat propeller and secured to the boat propeller shaft and the anti-biofouling structure positioned on the blades of the boat propeller.

FIG. 15 illustrates the protective enclosure element 64 in the fully extended position and placed over the propeller 16. FIG. 16 shows the addition of the anti-biofouling structure 20 to the propeller 16. In use, the protective enclosure element 64 and the anti-biofouling structure 20 can be secured to the necessary structures with the aid of a diver. For example, the diver encapsulates the protective enclosure element 64 over the propeller 16 by extending the protective enclosure element 64 from the first storage position to the second extendable position. The protective enclosure element 64 is secured to the exposed propeller shaft 18 through the securing element 82, including but not limited to a gasket such as a closed cell foam ring (not illustrated) and a circlip, see 82' FIG. 9, commonly used on agriculture equipment. The securing elements can be constructed of plastic or stainless steel materials and can be sized to fit specific sized shafts. The protective enclosure element 64 may also be designed to seal against itself through the use of various sealing methods such as snaps, buttons, or hook and loop fastening systems, such as VELCRO. In a particular embodiment, the securing end 80 of the protective enclosure element 64 is sealed with VELCRO type retention strips 88 and 90 which are attached to the outside perimeter of the protective enclosure element 64. This provides attachment of the protective enclosure element 64 around the propeller shaft.

Figure 13:
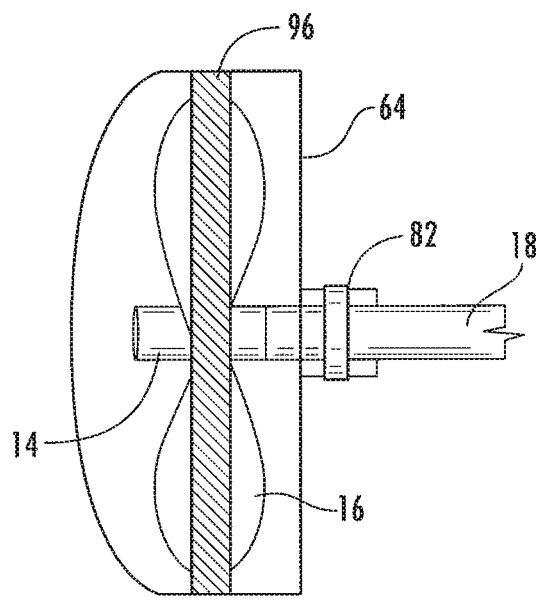
FIG. 13 illustrates the protective enclosure element with a stiffening plate.

The protective enclosure element 64 may also include a semi-rigid, rectangular plastic stiffening plate 96, see FIG. 13. The stiffening plate 96 is riveted to the inside of the protective enclosure element 64. The plate assists in defining the protective enclosure element 64 and will also facilitate the removal process by providing support for the device that triggers release of the protective enclosure element 64 from around the propeller. This balances and facilitates the removal of the protective enclosure element 64, thus reducing the likelihood of the device becoming ensnared in either the propeller blades or rudder appendages. The circlip 82', which maintains the protective enclosure element 64 seal around the propeller shaft 18, may be designed to have a looped portion. The VELCRO which is used to seal the forward end of the protective enclosure element 64 on both sides of the forward face also contains a looped portion. The looped portion can be used to clip the circlip together. This prevents the VELCRO connection from becoming unattached and secures the circlip. Once secured in place, the protective enclosure element 64 and the anti-biofouling structure 20, which has been fitted to the propellers 16, remain in place without the need for continuous monitoring and re-securing steps, thereby protecting the encapsulated structures from the aquatic environment without any additional efforts from the user.

Figure 14:
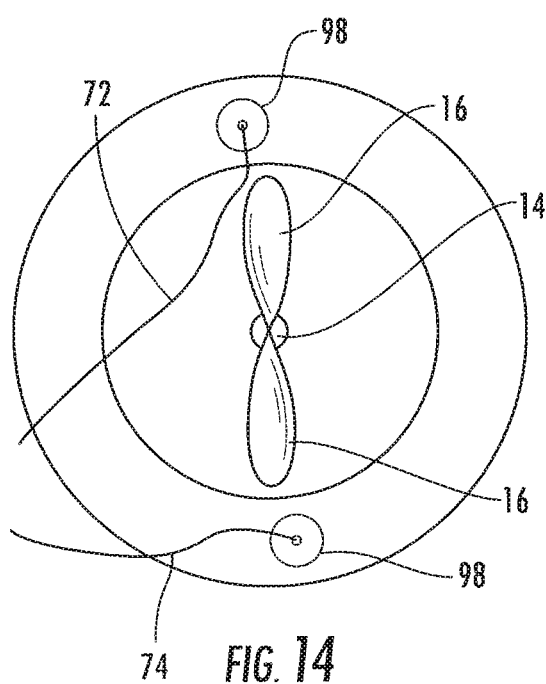
FIG. 14 is a frontal view of the protective enclosure element positioned over a boat propeller.

One of the advantages of the system as described herein is that the components of the system are designed for easy removal. The two cables 72 and 74 are positioned on the outside surface of the protective enclosure element 64 and are fed over the top of the propeller blades when the protective enclosure element 64 is fully extended. The two cables may be positioned at points which are 180 degrees from each other when facing the back side of the propeller. Each of the cables may simply be attached to the protective enclosure element 64 via stitching, gluing, or through the use of a small diameter, TEFLON-lined synthetic guide tube 98, see FIGS. 10 and 14. The tube can be secured at one or more points on each side of the outside perimeter of the protective enclosure element 64. The tubes can be designed to contain a 90 degree bend with an opening facing the aft and the other end facing the propeller shaft. The cables 72 and 74 are secured together with the attaching element 76 to form the single securing cable 78. The securing cable 78 is led aft and up over a portion of the boat, such as the swim platform or transom, and secured to the inside of the boat through a cleat on each side of the boat with slight tension. When the boat is at rest, the likelihood that the cable becomes entangled by an object and results in creating a strong enough tension so as to dislodge the securing devices is minimal.

Once the boat operator decides that the protective enclosure element 64 must be removed, the operator pulls upon the securing cable 78 with a backward force. Such a force simultaneously pulls on the circlip and releases the device from the propeller shaft. The backward force also releases the VELCRO connection, thereby releasing the protective enclosure element 64. The protective enclosure element 64 is now free to be pulled completely off the enclosed object, i.e. propeller 16. Once free from the propeller, the boat operator can start the engine, thereby creating rotational spin of the propellers. As the propellers rotate, the anti-biofouling sock 20 is expelled from the propellers into the water. The operator can then simply retrieve the expelled anti-biofouling sock 20 from the water. Alternatively, if the anti-biofouling sock 20 is made of a degradable material, the sock can be left safely in the water to naturally disintegrate.

FIGS. 17-19 illustrate an alternative embodiment of the anti-biofouling structure, illustrated generally as 100. In this embodiment, the structure 100 is formed from a first rigid member 102 and a second rigid member 104 interconnected to form a clam-shell configuration. Each of the rigid members 102 and 104 contain an interior 106 and 108 which is sized and shaped to house a propeller. The outer shell is preferably made from a material, such as plastics or a natural material, such as cotton, having a hardness to retain its shape. Coated into the plastic or cotton material is one or more anti-biofouling, biocide materials. Alternatively, or in combination, in a biocide paint may be used to coat the outer surfaces 110 and 112. In one embodiment, the bottom edge 114 of the first rigid member 102 and the bottom edge 116 of the second rigid member 104 are hingedly connected through a living hinge 118 and 120 or any other hinge mechanism which allows each of the halves to move relative to each other, thereby opening and closing about the hinge. Each of the rigid members 102 and 104 may further contain a cut-out section 122 and 124 which are sized and shaped to allow a rotor shaft to pass through when placed side by side.

Referring to FIG. 18, when the first rigid member 102 is aligned with the second rigid member 104, the cut out sections 122 and 124 form an opening 126. When the structure 100 is placed over a rotor, the shaft connecting to the rotor passes through the opening. To secure the first rigid member to the second rigid member, the top surface 128 of the first rigid member 102 and the top surface 130 of the second rigid member 104 contain one locking member of a locking mechanism. As illustrated, the top face 128 contains an eyelet 132 which is positioned to align with in a parallel fashion, or overlap, a second eyelet 134 attached to the top surface of 130 when the two rigid members are closed together. A securing member, illustrated herein as a cotter pin 136, may be used to secure the two members together. Preferably, the cotter pin 136 is secured to a portion of a lanyard 138. A second portion of the lanyard 138 is attached to either half of the clam shell halves. As shown in FIG. 18, the lanyard 138 attaches to the bottom surface area 140 of the first half 102 or the bottom surface 142 of the second half 104 through, for example, an eyelet 144. The amount of lanyard which attaches to the cotter pin 136 is preferably less than the amount of lanyard used to attach to the bottom. In this manner, pulling on the handle attached to the lanyard 138 results in pulling the pin 136 from the overlapping eyelets 132 and 134 first. As the lanyard 138 is continually pulled back, at some point a tension is formed on the part of the lanyard that is connected to either of the rigid members 102 or 104, resulting in the pulling apart of one or both of the rigid members 102 and 104. Although not illustrated, each of the halves may contain a weighted section to allow them to sink below the boat. Since they remain attached to the lanyard, the user can simply retrieve the halves by pulling on the lanyard 138. Alternative securing mechanisms, including buttons, snaps, zippers or other means known to one of skill in the art can be used as well.

Figure 20:
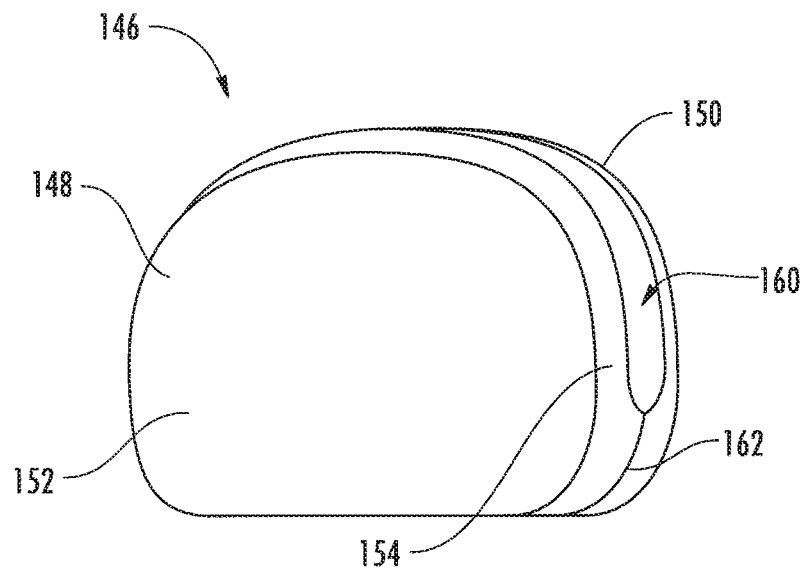
FIG. 20 is a side perspective view of the alternative embodiment of the anti-biofouling structure.
Figure 21:
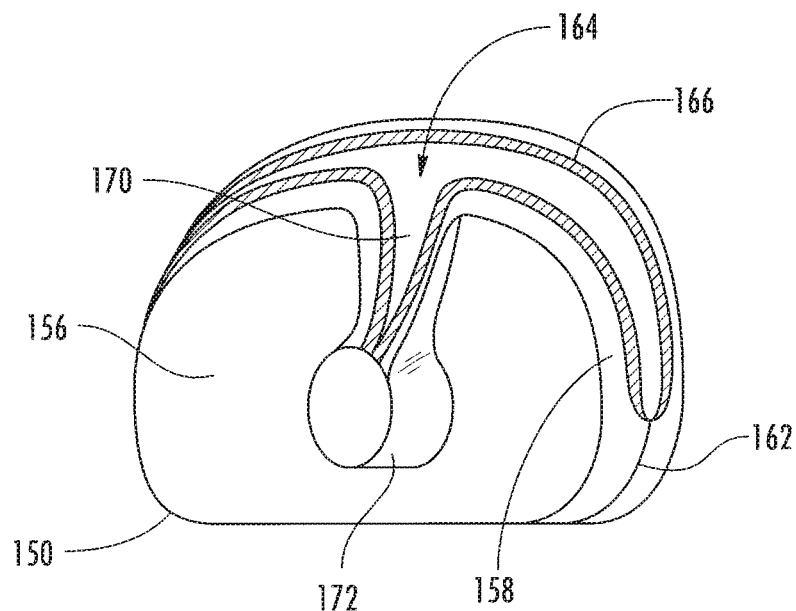
FIG. 21 is a rear perspective view of the alternative embodiment of the anti-biofouling structure shown in FIG. 20.
Figure 22:
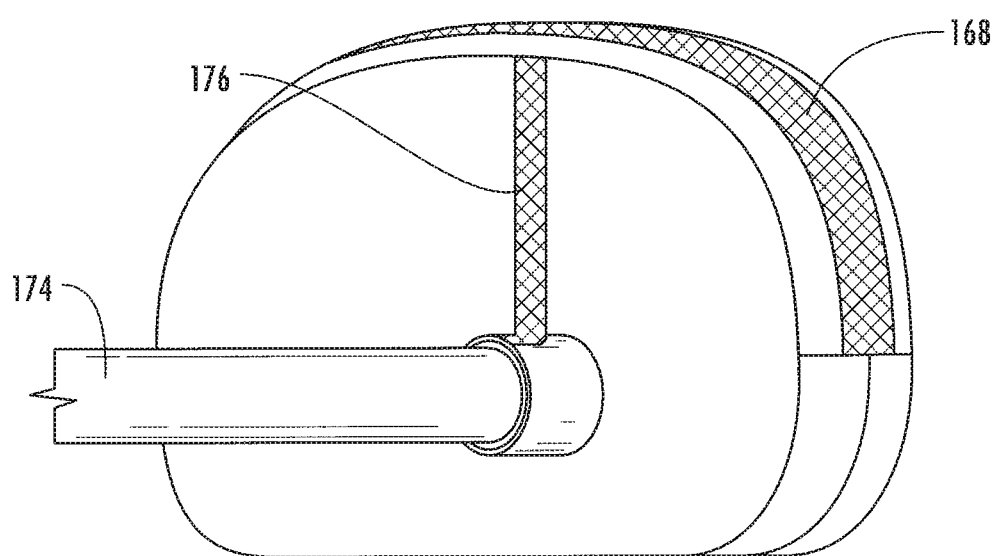
FIG. 22 is a rear perspective view of the alternative embodiment of the anti-biofouling structure shown in FIG. 20, illustrating the structure in a closed, sealed configuration.

Referring to FIGS. 20-22, an alternative embodiment of the anti-biofouling structure is shown and illustrated as a bag-like cover 146. The bag-like cover 146 is preferably made of a pliable plastic or natural fiber material which is impregnated, encapsulated, or coated with a biocide material. The bag-like cover 146 contains two panels 148 and 150, see FIGS. 20 and 21. Panel 148 contains a face 152 which forms the front portion of the bag-like cover 146 and an edge 154 which traverses the perimeter of the face 152. The panel 150 contains a face 156 which forms the back portion of the bag-like cover 146. An edge 158 traverses the perimeter of the face of 156. The panels 148 and 150 interconnect through edges 154 and 158 to form an interior portion 160. The interior portion 160 is sized and shaped to receive a structure, such as a boat propeller, which needs to be protected from the effects of biofouling. Preferably, the two panels 148 and 150 are partially interconnected through a fastening mechanism, such as stitching 162 or chemical means.

As illustrated in FIG. 21, a portion of the bag-like cover 146 does not provide for the panels 148 and 150 to be interconnected by stitching 162. This configuration provides for an opening 164. The opening 164 provides a means for the bag-like cover 146 to be arranged over a structure or object which needs to be protected from biofouling. Once secured over the object, bag-like cover 146 can be closed through securing members such as buttons, snaps, zippers, or other means known to one of skill in the art. In a preferred embodiment, the securing members are preferably a loop and hook type fastening system, i.e. VELCRO. Accordingly, a portion of the edges 154 and 158 or the faces 152 and 156 may contain the VELCRO loops 166 secured through, for example stitching or chemical fastening, their surfaces. An externally attached strap containing VELCRO hooks is used to fasten the edges 154 and 158 together. By placing edges 154 and 158 in close proximity, the strap 168 containing the VELCRO hooks is placed over the VELCRO loops 166 portions, see FIG. 22.

As illustrated in FIG. 21, the back face 156 contains a slitted portion 170 which terminates in a portion of the bag which extends outwardly facing cylindrical shape 172. The slitted portion 170 provides for the bag-like cover to enclose an object which contains portions which may not need to be covered. For example, the cylindrical shape 172 shown in FIG. 21 is designed to allow the bag-like cover 146 to enclose the propeller of the boat but allow the propeller shaft 174 to extend out. The portions of the face 156 that defines the slitted areas can be covered with VELCRO loops as described above. Aligning the areas in close proximity allows a second strap 176 containing VELCRO hooks to be placed on top to secure them together around the circumference of the propeller shaft 174. Each of the straps 168 and 176 may contain one or more attached O-rings (not illustrated). One or more lanyards (not illustrated) may be attached to the O-rings. Pulling the lanyards away from the cover provides a force that results in removal of the straps 168 and 176 from the VELCRO loops 166. Fastened to the interior portion of the cover 146 may be one or more D-rings (not illustrated) which preferably attach to one or both straps 168 and 176 through, for example, stitching. Once coupled to the D-rings, the straps 168 and/or 176 remain connected to the bag thereby reducing the risk that they will be displaced. One or more openings along the surface of the bag may be utilized to allow the straps to exit the interior portion and couple to the VELCRO loops 166. Once the straps are removed from the VELCRO loops 166, the bag is partially opened and it can be removed from covering the object.

Referring to FIGS. 23-25, an alternative embodiment of the anti-biofouling structure is shown and illustrated as bag 178. The bag 178 is preferably constructed of a collapsible plastic material, similar to a standard garbage bag, and is impregnated or coated with a biocide material. The bag 178 contains a main body comprising an opening which is sized and shaped to allow a structure to be stored within the interior portion 184. The outer edges 186 and 184 may be made of a stronger material than that of the body to allow the bag 178 to maintain some shape. Tightening members, illustrated herein as drawstring 190 and 192, are used to enclose the bag 178 over the object. Drawstring 190 and 192 are preferably constructed in such a manner that, as the first drawstring 190 is pulled toward the second drawstring 192, opening 182 is reduced. Additionally, the drawstring 190 and 192, when pulled together maintain a tension so that when they are not secured together, they retract back to their original, non-pulled state. The drawstrings 190 and 192 contain eyelets 194 and 196 which align together when the two drawstrings are pulled toward each other. A securing member, such as a cotter pin 198 is used to secure the drawings together. In a similar manner, as described before, the cotter pin 198 can be secured to a string 200. The opposite end of the string 200 may be attached to the bag 178 at a canvas strap 202. Pulling on the canvas strap 202 results in dislodging the cotter pin 198 from the eyelets 194 and 196. Once the eyelets are no longer secured to each other, the drawstrings 190 and 192 retract, opening the bag and exposing object, illustrated herein, as a boat propeller 204, see FIG. 25.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed:

1. An anti-biofouling device for securement around or onto an object exposed to an aquatic environment, the device comprising:

a flexible material formed from a plurality of interwoven fibers that form a lattice-like or mesh configuration that allows passage of at least some of the aquatic environment therethrough;

one or more securing members connected to the flexible material and configured to enable securement around or onto the object exposed to the aquatic environment; and at least one anti-fouling agent applied to, coated on, or embedded in the plurality of interwoven fibers that form the lattice-like or mesh configuration of the flexible material, wherein the lattice-like or mesh configuration of the flexible material still enables passage of the at least some of the aquatic environment therethrough, and such that the at least some of the aquatic environment passing through the lattice-like or mesh configuration interacts with the at least one anti-fouling agent, wherein, when the flexible material is secured around or onto the object, the flexible material provides a protective enclosure within the aquatic environment for at least a portion of the object, wherein at least one of the flexible material or the at least one anti-fouling agent of the protective enclosure acts on the at least some of the aquatic environment that has passed through the protective enclosure to the object so as to reduce formation of biofouling organisms on the object exposed to the at least some of the aquatic environment.

2. The anti-biofouling device of claim 1, wherein the flexible material is formable such that, when the flexible material is secured around or onto the object, the flexible material is capable of mirroring a contour of the object.

3. The anti-biofouling device of claim 1, wherein the flexible material forms an expandable/collapsible body portion for fitting at least partially around the object.

4. The anti-biofouling device of claim 1, wherein the one or more securing members are configured for securement around or onto the object with the flexible material wrapped around the object.

5. The anti-biofouling device of claim 1, wherein the flexible material is formed of synthetic fiber, natural fiber, metal, or combinations thereof.

6. The anti-biofouling device of claim 1, wherein the one or more securing members include at least one of hook and loop type fasteners, snaps, buttons, glue strips, clasps, clips, or zippers.

7. The anti-biofouling device of claim 1, wherein the protective enclosure is in the form of a bag or bag-like cover.

8. The anti-biofouling device of claim 1, wherein the flexible material is formed from a rolled-up sheet.

9. The anti-biofouling device of claim 1, wherein the at least one anti-fouling agent is contained within one or more strips attached to the flexible material.

10. The anti-biofouling device of claim 1, wherein the at least one anti-fouling agent is microencapsulated.

11. The anti-biofouling device of claim 1, wherein the at least one anti-fouling agent is applied to the flexible material via a spray-on application.

12. A system for reducing formation of biofouling organisms on an object exposed to an aquatic environment, the system comprising:

a flexible material formed from a plurality of interwoven fibers that form a lattice-like or mesh configuration that allows passage of at least some of the aquatic environment therethrough;

one or more securing members connectable to the flexible material and configured to enable securement around or onto the object exposed to the aquatic environment; and at least one anti-fouling agent applied to or coated on the lattice-like or mesh configuration of the flexible material, wherein the lattice-like or mesh configuration of the flexible material still enables passage of the at least some of the aquatic environment therethrough with the anti-fouling agent applied thereto or coated thereon, and such that the at least some of the aquatic environment passing through the lattice-like or mesh configuration interacts with the at least one anti-fouling agent, wherein, when the flexible material is secured around or onto the object, the flexible material provides a protective enclosure within the aquatic environment for at least a portion of the object, wherein at least one of the flexible material or the at least one anti-fouling agent of the protective enclosure acts on the at least some of the aquatic environment that has passed through the protective enclosure to the object so as to reduce formation of biofouling organisms on the object exposed to the at least some of the aquatic environment, wherein the flexible material is formable such that, when the flexible material is secured around or onto the object, the flexible material is capable of mirroring a contour of the object.

13. The system of claim 12, wherein the flexible material forms an expandable/collapsible body portion for fitting at least partially around the object.

14. The system of claim 12, wherein the flexible material is in the form of a rolled-up sheet.

15. A rolled-up sheet of flexible material used for forming an anti-biofouling device for securement around or onto an object exposed to an aquatic environment, the rolled-up sheet comprising:

the flexible material formed from a plurality of interwoven fibers that form a lattice-like or mesh configuration that allows passage of at least some of the aquatic environment therethrough, wherein the flexible material includes at least one anti-fouling agent applied to, coated on, or embedded in the plurality of interwoven fibers or the lattice-like or mesh configuration of the flexible material, wherein the lattice-like or mesh configuration of the flexible material still enables passage of the at least some of the aquatic environment therethrough, and such that the at least some of the aquatic environment passing through the lattice-like or mesh configuration interacts with the at least one anti-fouling agent, wherein, when the flexible material is secured around or onto the object, the flexible material provides a protective enclosure within the aquatic environment for at least a portion of the object, wherein at least one of the flexible material or the at least one anti-fouling agent of the protective enclosure acts on the at least some of the aquatic environment that has passed through the protective enclosure to the object so as to reduce formation of biofouling organisms on the object exposed to the at least some of the aquatic environment.

16. The rolled-up sheet of claim 15, wherein the flexible material is formable such that, when the flexible material is secured around or onto the object, the flexible material is capable of mirroring a contour of the object.

17. The rolled-up sheet of claim 15, wherein the flexible material is formed of synthetic fiber, natural fiber, metal, or combinations thereof.

* * * * *